(12) United States Patent
Mollov et al.

(10) Patent No.: US 7,095,028 B2
(45) Date of Patent: Aug. 22, 2006

(54) MULTI-SLICE FLAT PANEL COMPUTED TOMOGRAPHY

(75) Inventors: Ivan Mollov, Cupertino, CA (US); Richard E. Colbeth, Los Altos, CA (US)

(73) Assignee: Varian Medical Systems, Palo Alto, CA (US)

( * ) Notice: Subject to any disclaimer, the term of this patent is extended or adjusted under 35 U.S.C. 154(b) by 92 days.

(21) Appl. No.: 10/687,552

(22) Filed: Oct. 15, 2003

(65) Prior Publication Data

US 2005/0082488 A1  Apr. 21, 2005

(51) Int. Cl.
  *G21K 1/12*  (2006.01)
(52) U.S. Cl. ............... 250/370.09; 250/369; 378/19
(58) Field of Classification Search ........... 250/370.09, 250/370.08, 370.11; 378/98.8, 19
  See application file for complete search history.

(56) References Cited

U.S. PATENT DOCUMENTS

| | | | |
|---|---|---|---|
| 4,191,856 A | 3/1980 | Nagano et al. | |
| 4,216,435 A | 8/1980 | Ahmed | |
| 4,220,873 A | 9/1980 | Giordano | |
| 4,366,522 A | 12/1982 | Baker | |
| 4,572,967 A | 2/1986 | Metz | |
| 4,596,958 A | 6/1986 | Graeme et al. | |
| 4,672,454 A | 6/1987 | Canella et al. | |
| 4,727,506 A | 2/1988 | Fling | |
| 4,740,722 A | 4/1988 | Furuhata | |
| 4,746,814 A | 5/1988 | Shigekane | |
| 4,804,863 A | 2/1989 | Welland et al. | |
| 5,130,567 A | 7/1992 | Rutten et al. | |
| 5,130,798 A | 7/1992 | Christopher | |
| 5,148,121 A | 9/1992 | Uchida | |
| 5,159,341 A | 10/1992 | McCartney et al. | |
| 5,170,115 A | 12/1992 | Kashiwabara et al. | |
| 5,184,018 A | 2/1993 | Conrads et al. | |
| 5,262,649 A | 11/1993 | Antonuk et al. | |
| 5,304,853 A | 4/1994 | Choi | |
| 5,331,222 A | 7/1994 | Lin et al. | |
| 5,352,987 A | 10/1994 | Harvey | |
| 5,355,035 A | 10/1994 | Vora et al. | |

(Continued)

FOREIGN PATENT DOCUMENTS

EP  0 159 654 B1  1/1991

(Continued)

OTHER PUBLICATIONS

Boyer, A.L. et al. A Review of Electronic Portal Imaging Devices (EPIDS) *Med. Phys.* (Jan./Feb. 1992) 19(1):1-16.

(Continued)

*Primary Examiner*—David P. Porta
*Assistant Examiner*—Faye Polyzos
(74) *Attorney, Agent, or Firm*—Bingham McCutchen LLP (57) ABSTRACT

A method for collecting signals from a detector that has a plurality of lines of image elements includes sending a control signal to a gate driver to select transistor gates for two or more lines of image elements, and simultaneously passing signals from the two or more lines of image elements to charge amplifiers that are coupled to the image elements. A method for collecting signals from a detector that has a plurality of imagers is provided. Each of the imagers has a plurality of lines of image elements. The method includes sending a control signal to a gate driver to select one or more lines of image elements on each of the plurality of the imagers, and simultaneously passing signals from the selected one or more lines of image elements on each of the plurality of imagers to charge amplifiers that are coupled to the image elements.

50 Claims, 7 Drawing Sheets

U.S. PATENT DOCUMENTS

| | | | |
|---|---|---|---|
| 5,363,055 | A | 11/1994 | Ribner |
| 5,400,083 | A | 3/1995 | Mizusawa |
| 5,430,400 | A | 7/1995 | Herlein et al. |
| 5,442,407 | A | 8/1995 | Iu |
| 5,459,320 | A * | 10/1995 | Danet et al. ........... 250/363.04 |
| 5,465,284 | A | 11/1995 | Karellas |
| 5,489,910 | A | 2/1996 | Kuwata et al. |
| 5,506,880 | A | 4/1996 | Scardino et al. |
| 5,508,751 | A | 4/1996 | Nitta |
| 5,576,646 | A | 11/1996 | Rezzi et al. |
| 5,581,274 | A | 12/1996 | Tagawa |
| 5,589,847 | A | 12/1996 | Lewis |
| 5,657,400 | A | 8/1997 | Granfors et al. |
| 5,689,197 | A | 11/1997 | Sugawara |
| 5,717,457 | A | 2/1998 | Morimoto |
| 5,739,803 | A | 4/1998 | Neugebauer |
| 5,801,571 | A | 9/1998 | Allen et al. |
| 5,864,146 | A | 1/1999 | Karellas |
| 5,872,470 | A | 2/1999 | Mallinson et al. |
| 5,953,060 | A | 9/1999 | Dierickx |
| 5,970,115 | A | 10/1999 | Colbeth et al. |
| 6,084,461 | A | 7/2000 | Colbeth et al. |
| 6,118,438 | A | 9/2000 | Ho |
| 6,259,489 | B1 | 7/2001 | Flannaghan et al. |
| 6,310,567 | B1 | 10/2001 | Copley et al. |
| 6,331,844 | B1 | 12/2001 | Okumura et al. |
| RE37,536 | E * | 2/2002 | Barnes ................... 250/361 R |
| 6,359,607 | B1 | 3/2002 | Yanagi et al. |
| 6,424,750 | B1 | 7/2002 | Colbeth et al. |
| 8,445,784 | | 9/2002 | Gohno et al. |
| 6,469,740 | B1 | 10/2002 | Kuroda et al. |
| 6,486,808 | B1 | 11/2002 | Seppi et al. |
| 6,535,254 | B1 | 3/2003 | Olsson et al. |
| 6,587,142 | B1 | 7/2003 | Kozlowski et al. |
| 6,653,992 | B1 | 11/2003 | Colbeth et al. |
| 6,707,876 | B1 * | 3/2004 | Tanigawa ................... 378/19 |
| 6,718,069 | B1 | 4/2004 | Mollov et al. |
| 6,744,912 | B1 | 6/2004 | Colbeth et al. |
| 2002/0191737 | A1 | 12/2002 | Tanigawa |

FOREIGN PATENT DOCUMENTS

| | | |
|---|---|---|
| EP | 0 776 124 A2 | 5/1997 |
| EP | 0 776 124 A3 | 5/1997 |

OTHER PUBLICATIONS

Brailean, J.C. Et al. "Noise Reduction Filters for Dynamic Image Sequences: A Review" *Proceedings of the IEEE* (Sep. 1995) 83(9):1272-1292.

Fujieda, I. et al. "Two Operation Modes of 2D a-Si Sensor Arrays for Radiating Imaging" *J. Non-Crystalline Solids 173 & 138* (1991) pp. 1321-1324.

Schiebel, U. et al. "Fluoroscopic X-Ray Imaging with Amorphous Silicon Thin-Film Arrays" *SPIE Vol. 2163 Physics of Medical Imaging* (1994) pp. 129-140.

International search Report dated Sep. 6, 2005 (PCT/US04734111).

* cited by examiner

MULTI-SLICE FLAT PANEL COMPUTED TOMOGRAPHY

BACKGROUND OF THE INVENTION

1. Field of the Invention

This invention relates generally to systems and methods for image acquisition and, more specifically, to systems and methods for collecting computed tomography (CT) image data.

2. Background of the Invention

Computed tomography is an imaging technique that has been widely used in the medical field. In a procedure for computed tomography, an x-ray source and a detector apparatus are positioned on opposite sides of a portion of a patient under examination. The x-ray source generates and directs a x-ray beam towards the patient, while the detector apparatus measures the x-ray absorption at a plurality of transmission paths defined by the x-ray beam during the process. The detector apparatus produces a voltage proportional to the intensity of incident x-rays, and the voltage is read and digitized for subsequent processing in a computer. By taking thousands of readings from multiple angles around the patient, relatively massive amounts of data are thus accumulated. The accumulated data are then analyzed and processed for reconstruction of a matrix (visual or otherwise), which constitutes a depiction of a density function of the bodily section being examined. By considering one or more of such sections, a skilled diagnostician can often diagnose various bodily ailments such as tumors, blood clots, etc.

A problem associated with existing CT imaging systems is that a patient may not feel comfortable confined within a gantry opening, especially when the image data collection procedure takes too long. Mechanical configuration and/or regulatory rules may limit the rotation rate of a gantry on which the x-ray source and the image detector are mounted. Some of the existing CT imaging devices have gantry speed that is limited to one rotation per minute. Although some of the existing CT scanners can be configured to rotate about a patient faster, the volumetric data set generated from such scanners may have motion artifacts between slices.

Another problem associated with existing CT imaging systems is that a slice thickness is generally larger than a resolution of a pixel within a slice. For example, an existing CT imaging system may generate a slice every 1 centimeter, while a resolution of a pixel within a slice is 0.5 millimeter. In order to create better resolution between slices, scanners have been developed that has an increased number of detectors in the Z-axis (axis of rotation) direction. However, increasing the number of detectors in the Z-axis increases the manufacturing cost of the detector, which is already quite expensive as it is based on traditional single crystal silicon electronics coupled to x-ray converters.

For the foregoing, improved apparatus and method for collecting CT image data and generating CT images would be desirable.

SUMMARY OF THE INVENTION

In accordance with some embodiments of the invention, a radiation projection detector for generating signals in response to a radiation beam is provided. The detector has a first imager that includes a conversion layer configured to generate light photons in response to a radiation, a photo detector array aligned with the conversion panel, the photo detector array having a plurality of lines of detector elements, and an access circuit coupled to the photo detector array and configured to collect signals from two or more of the lines of detector elements simultaneously. By collecting signals from two or more lines of detector elements simultaneously or in parallel, the time it takes to readout signals from all lines of the detector elements in the detector can be reduced. This in turn, improves a frame rate of the detector. In some embodiments, the radiation projection detector includes a second imager. In such cases, the access circuit is configured to collect signals from the first imager and the second imager simultaneously. The plurality of the imagers provides another level of multiplexing in that signals from one or more lines of detector elements in the first imager can be read simultaneously with signals from one or more lines of detector elements in the second imager.

In accordance with other embodiments of the invention, a radiation projection detector for generating signals in response to a radiation beam is provided. The detector has a first imager that includes a photoconductor layer configured to generate a charge in response to a radiation, a detector array aligned with the photoconductor layer, the detector array having a plurality of lines of detector elements, and an access circuit coupled to the detector array and configured to collect signals from two or more of the lines of detector elements simultaneously. By collecting signals from two or more lines of detector elements simultaneously or in parallel, the time it takes to readout signals from all lines of the detector elements in the detector can be reduced. This in turn, improves a frame rate of the detector. In some embodiments, the radiation projection detector includes a second imager. In such cases, the access circuit is configured to collect signals from the first imager and the second imager simultaneously. The plurality of the imagers provides another level of multiplexing in that signals from one or more lines of detector elements in the first imager can be read simultaneously with signals from one or more lines of detector elements in the second imager.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present invention are obtained, a more particular description of the present invention briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention.

Figure 1:
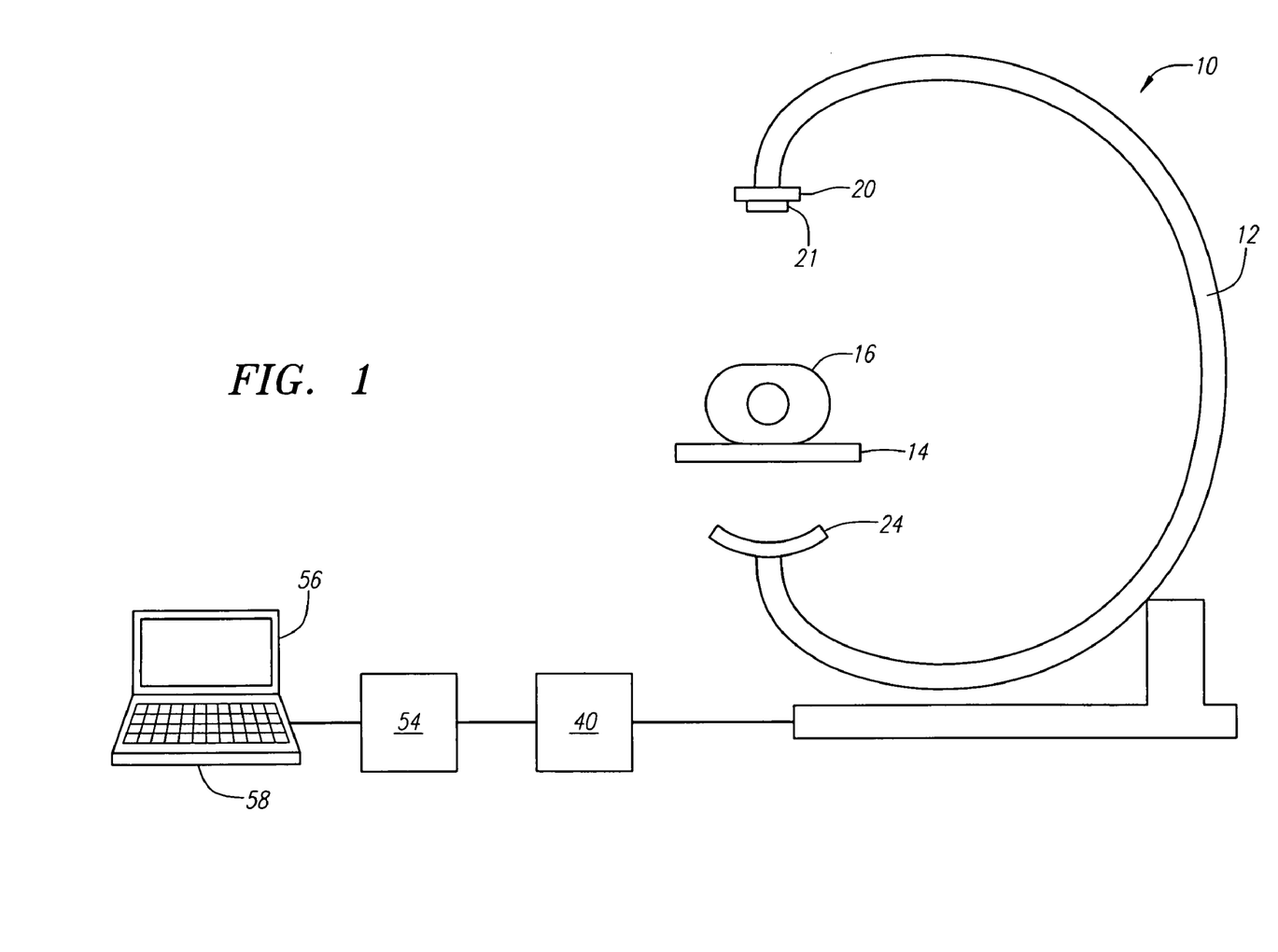
FIG. 1 illustrates a computed tomography system in which embodiments of the present invention may be implemented.

Referring now to the drawings, in which similar or corresponding parts are identified with the same reference numeral, FIG. 1 illustrates a computed tomography (CT) image acquisition system 10, which includes a detector 24 constructed in accordance with an embodiment of the present invention. The system 10 includes a gantry 12, and a panel 14 for supporting a patient 16. The gantry 12 includes an x-ray source 20 that projects a beam of x-rays, such as a fan beam or a cone beam, towards the detector 24 on an opposite side of the gantry 12 while the patient 16 is positioned at least partially between the x-ray source 20 and the detector 24. The x-ray source 20 may include a collimator 21 for adjusting a shape of the x-ray beam. The detector 24 has a plurality of sensor elements configured for sensing a x-ray that passes through the patient 16. Each sensor element generates an electrical signal representative of an intensity of the x-ray beam as it passes through the patient 16.

In the illustrated embodiment, the CT image acquisition system 10 also includes a processor 54, a monitor 56 for displaying data, and an input device 58, such as a keyboard or a mouse, for inputting data. The processor 54 is coupled to a gantry rotation control 40. The rotation of the gantry 12 and the operation of the x-ray source 20 are controlled by the gantry rotation control 40, which provides power and timing signals to the x-ray source 20 and controls a rotational speed and position of the gantry 12 based on signals received from the processor 54. Although the control 40 is shown as a separate component from the gantry 12 and the processor 54, in alternative embodiments, the control 40 can be a part of the gantry 12 or the processor 54.

During a scan to acquire x-ray projection data (i.e., CT image data), the x-ray source 20 projects a beam of x-rays towards the detector 24 on an opposite side of the gantry 12, while the gantry 12 rotates about the patient 16. In one embodiment, the gantry 12 makes a 360° rotation around the patient 16 during image data acquisition. Alternatively, if a full cone detector is used, the system 10 may acquire data while the gantry 12 rotates 180° plus the angle of the beam pattern. Other angles of rotation may also be used, depending on the particular system being employed. In one embodiment, the detector 24 is configured to generate at least 900 frames of images in less than 1 second. In such case, the gantry 12 only needs to rotate around the patient 16 once in order to collect sufficient amount of image data for reconstruction of computed tomography images. In other embodiments, the detector 24 may be configured to generate frames at other speeds.

Figure 2:
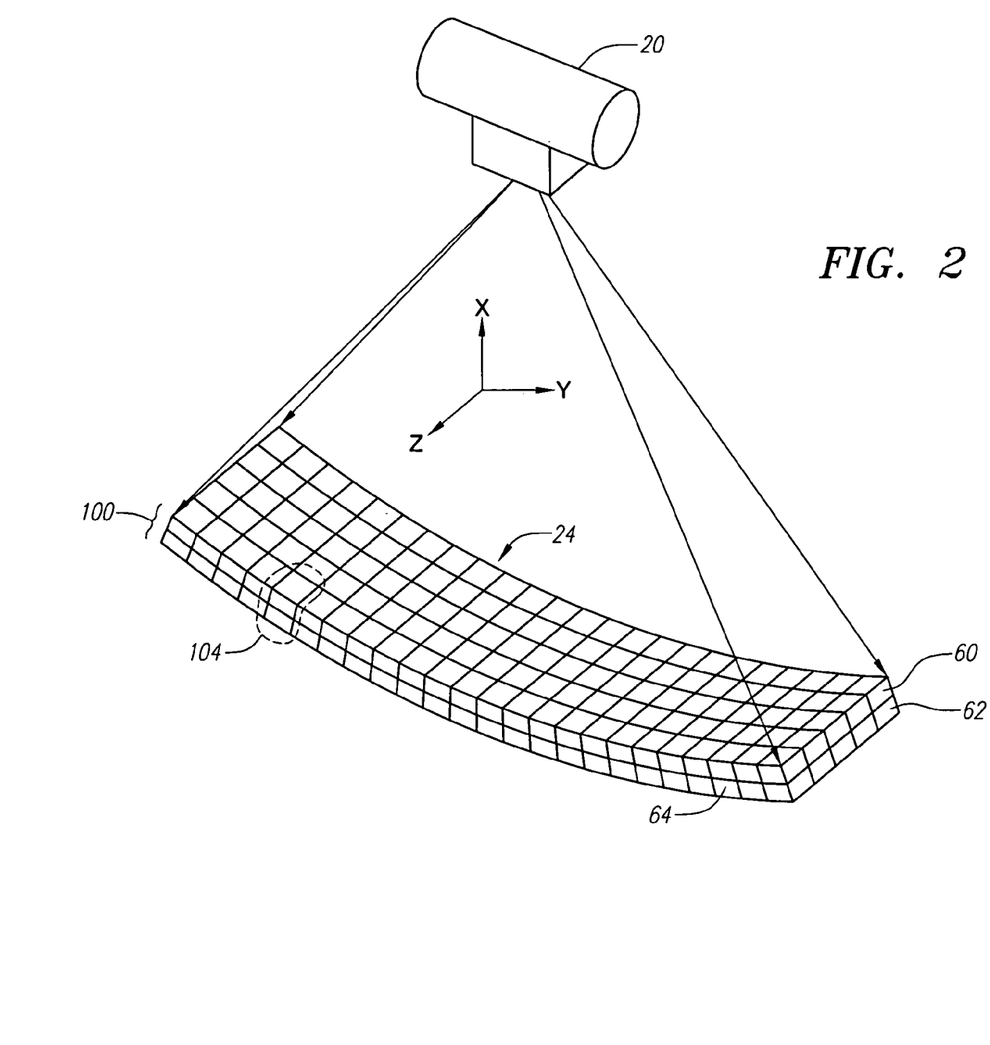
FIG. 2 shows an embodiment of the detector of FIG. 1.

FIG. 2 shows a detector 24 constructed in accordance with an embodiment of the present invention. As shown in FIG. 2, the detector 24 comprises an imager 100 that includes a x-ray conversion layer 60 made from a scintillator element, such as Cesium Iodide (CsI), and a photo detector array 62 (e.g., a photodiode layer) coupled to the x-ray conversion layer 60. The x-ray conversion layer 60 generates light photons in response to x-ray radiation, and the photo detector array 62, which includes a plurality of detector elements 64, is configured to generate electrical signal in response to the light photons from the x-ray conversion layer 60. In the illustrated embodiment, both the x-ray conversion layer 60 and the photo detector array 62 are pixilated, thereby forming a plurality of imaging elements 104. However, the x-ray conversion layer 60 may be non-pixilated in an alternative embodiment. As shown in FIG. 2, the imager 100 has a curvilinear surface (e.g., a partial circular arc). Such configuration is beneficial in that each of the imaging elements 104 of the imager 100 is located substantially the same distance from the x-ray source 20. In an alternative embodiment, the imager 100 may have a rectilinear surface or a surface having other profiles. In the illustrated embodiment, each image element 104 (or pixel) has a cross sectional dimension that is approximately 200 microns or more, and more preferably, approximately 300 microns or more. However, image elements having other dimensions may also be used. The imager 100 can be made from amorphous silicon, crystal and silicon wafers, crystal and silicon substrate, or flexible substrate (e.g., plastic), and may be constructed using flat panel technologies or other techniques known in the art of making imaging device.

Figure 3:
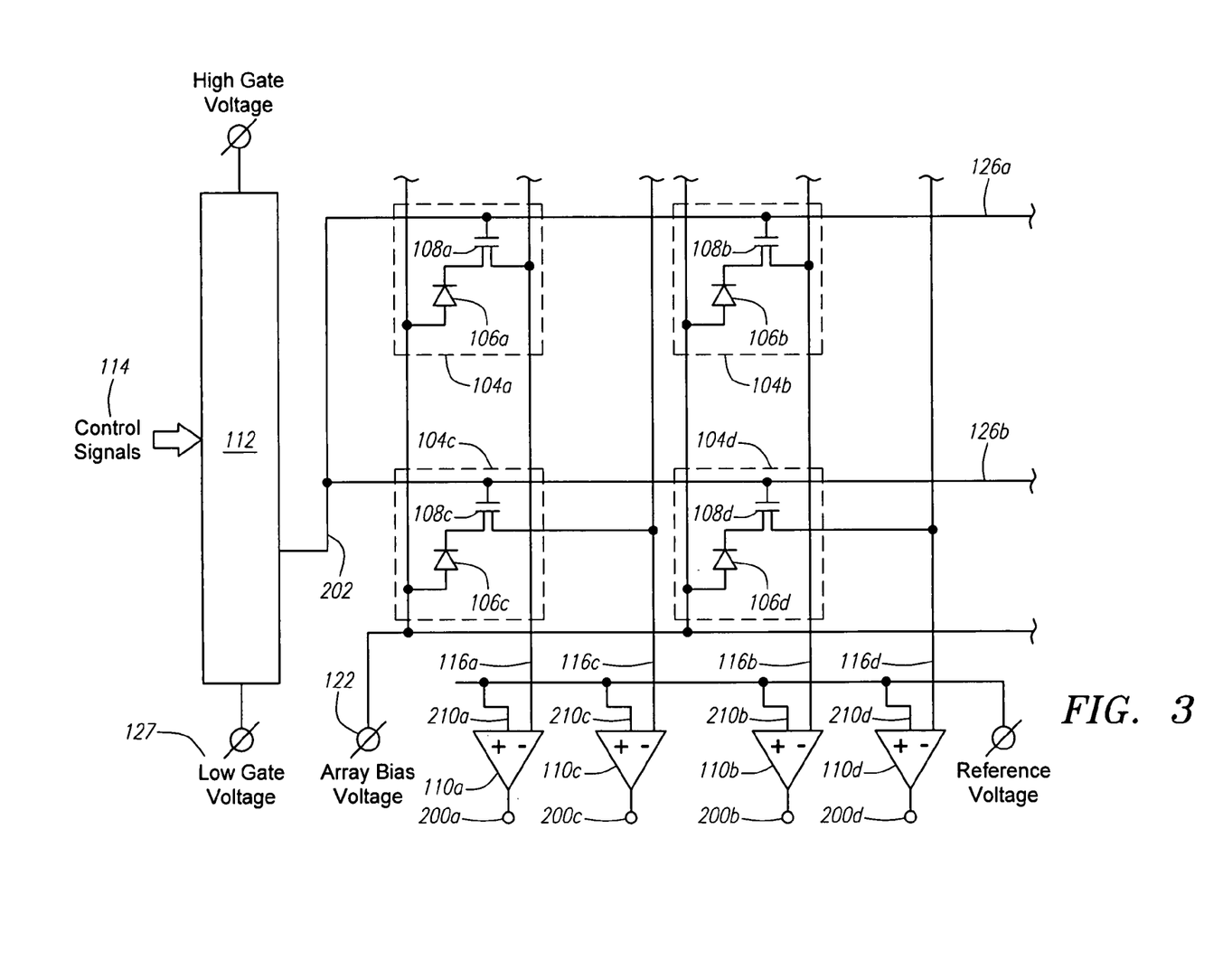
FIG. 3 shows one configuration of electrical components for the imager of FIG. 2 constructed in accordance with an embodiment of the present invention, particularly showing the imager having a two-row readout configuration.

FIG. 3 depicts one configuration of electrical components for the imager 100 in accordance with an embodiment of the present invention. The imager 100 includes a plurality of the image elements 104, each of which comprises a photodiode 106 (forming part of the detector element 64) that generates an electrical signal in response to a light input. The photodiode 106 receives light input from the x-ray conversion layer 60 that generates light in response to x-rays. The photodiodes 106 are connected to an array bias voltage 122 to supply a reverse bias voltage for the image elements. A transistor 108 (such as a thin-film N-type FET) functions as a switching element for the image element 104. When it is desired to capture image data from the image elements 104, control signals 114 are sent to a gate driver 112 to "select" the gate(s) of transistors 108. The gate driver 112 is connected to a low gate voltage 127 that drives the gate control lines. Electrical signals from the photodiodes 106 are passed through lines 116 to corresponding charge amplifiers 110. The output of the charge amplifiers 110 is sent to a "sample and hold" stage for further image processing/display. In one embodiment, the gate driver 112 is a part of an access circuit, which may be secured to an edge of the imager 100. The access circuit may also include the charge amplifiers 110. While FIG. 3 only shows four image elements 104a–104d, those skilled in the art understands that the imager 100 may include many such image elements 104, depending upon the size and resolution of the imaging device. In addition, although only two lines 126a and 126b of image elements 104 are shown, the imager 100 may include more than two lines 126 of image elements 104.

The imager 100 performs simultaneous sampling of image data from image elements 104 in a correlated manner. In the illustrated embodiment, the imager 100 includes corresponding amplifiers 110 for each of the image elements 104 on the two lines 126a and 126b, thereby allowing image data from the two lines 126a and 126b of image elements 104 to be collected or read simultaneously (i.e., at substantially the same time). All the switching transistors 108a–108d for image elements 104a–104d on the two lines 126a and 126b are tied to the same control line 202 extending from gate driver 112. When the image data for the two lines 126a and 126b of image elements 104 are desired, control signals 114 are sent to the gate driver 112 to select the transistor gates for the desired lines (e.g., 126a and 126b) of image elements. The electrical signals from the entire lines 126a and 126b of image elements are passed to their corresponding charge amplifiers 110, which output signal data to the subsequent sampling stage. If the imager 100 has more than two lines 126 of image elements 104, to form an entire image frame, image data are collected two lines at a time until all lines 126 of image elements 104 on the imager 100 have been sampled. For a given configuration of the imager 100, a signal readout time for each line 126 of image elements 104 depends on the time it takes to turn on a pixel and discharge a corresponding signal, and is generally fixed (e.g., approximately 40 microseconds per second). As such, by configuring the imager 100 to allow signals from two or more lines of image elements 104 to be read simultaneously or in parallel, the time it takes to readout signals from all the lines 126 of the imager can be reduced. This in turn, improves a frame rate (i.e., number of frames that can be generated by the imager 100 per second) of the imager 100.

Figure 4:
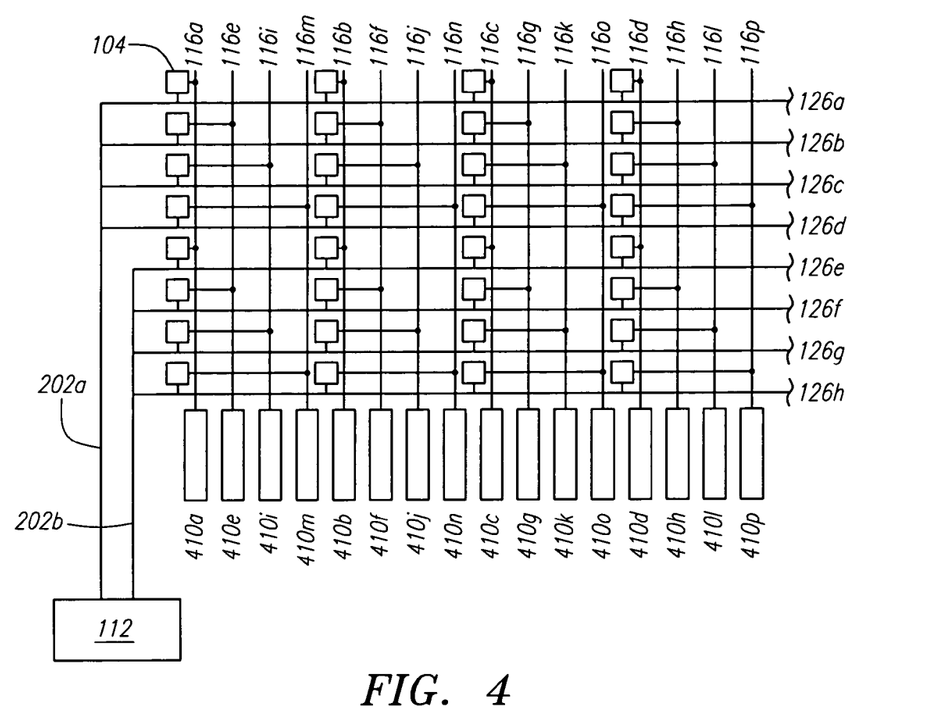
FIG. 4 shows a variation of the flat panel imager of FIG. 3, particularly showing the imager having a four-row read-out configuration.

Although the above embodiment of the imager 100 has been described as having a two-line readout configuration, in alternative embodiments, the imager 100 may have a configuration that allows signals be collected from more than two lines of image elements 104 at a time. FIG. 4 shows a variation of the imager 100 which has a four-line readout configuration. As shown in FIG. 4, image elements 104 on every four lines (e.g., 126a–126d or 126e–126h) are connected to corresponding devices, such as amplifiers 110a–110p (not shown) through connecting lines 126a–116p and connecting pads 410a–410p, respectively. In the illustrated embodiment, all the switching transistors for image elements 104 on the four lines 126a–126d are tied to the same control line 202a extending from the gate driver 112, and all the switching transistors for image elements 104 on the four lines 126e–126h are tied to the same control line 202b extending from the gate driver 112. When the image data for the four lines 126a–d of image elements 104 are desired, control signals 114 are sent to the gate driver 112 to select (via the control line 202a) the transistor gates for the four lines 126a–126d of image elements 104. The electrical signals from the image elements 104 on the four lines 126a–d are passed to their corresponding charge amplifiers 110a–p, which output signal data to the subsequent sampling stage. To collect signals from the next four lines 126e–126h of image elements 104, control signals 114 are sent to the gate driver 112 to select (via the control line 202b) the transistor gates for the four lines 126e–126h of image elements 104. To form an entire image frame, image data are collected four lines at a time until all lines of image elements 104 on the imager 100 have been sampled.

As shown in FIG. 4, the number of connecting pads 410 or interconnects can be accommodated within a given length is limited by the size of the connecting pads 410 and a spacing between the connecting pads 410. The number of connecting pads 410 that can be fitted within a given length may limit the number of lines 126 of image elements 104 that can be connected to corresponding devices, such as the amplifiers 110. In one embodiment, to increase the interconnects of the imager 100, each image element 104 may be made larger, or alternatively, the number of image elements 104 along each line 126 may be reduced. For example, in one embodiment, each image element 104 may have a cross sectional dimension that is larger than approximately 300 microns, or more preferably, more than approximately 400 microns. However, image elements having other dimensions may also be used. Those skilled in the art understand that the larger the image element 104, and/or the fewer the number of the image elements 104 along each line 126, the higher the interconnects, and the higher the frame rate that can be achieved.

Figure 5:
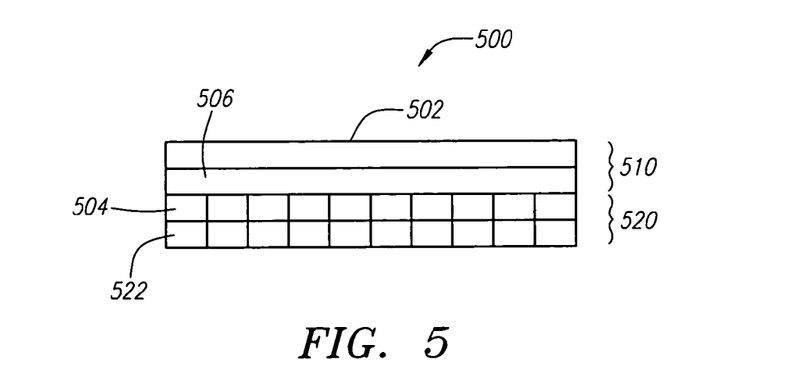
FIG. 5 shows a variation of the detector of FIG. 2, particularly showing the imager having a layer of photoconductor.

Although the imager 100 has been described as having the x-ray conversion layer 60, in alternative embodiments, the imager 100 may use different detection schemes. For example, in alternative embodiments, instead of having the x-ray conversion layer 60, the imager 100 may include a photoconductor, which generates electron-hole-pairs or charges in response to x-ray. FIG. 5 schematically shows an imager 500 constructed in accordance with alternative embodiments of the present invention. The flat panel imager 500 includes an x-ray conversion panel 510 aligned with a detector array 520. The x-ray conversion panel 510 includes a first electrode 502, a second electrode 504, and a photoconductor 506 secured between the first electrode 502 and the second electrode 504. The electrodes 502 and 504 may be made from a wide variety of materials, such as silver, chromium, aluminum, gold, nickel, vanadium, zinc, palladium, platinum, carbon, etc., and alloys of these materials. The photoconductor 506 can be made from a variety of materials, such as mercuric Iodide (HgI2), Lead Iodide (PbI2), Bismuth Iodide (BiI3), Cesium Iodide (CsI), Cadmium Zinc Telluride (CdZnTe), Amorphous Selenium (a-Se), or equivalent thereof. Other materials known in the art may also be used. The photoconductor 506 may be a single or poly-crystalline layer. The photoconductor 506 is preferably deposited by physical vapor deposition (PVD) or particle in binder process (PIB). Alternatively, if the photoconductor 506 is deposited on a separate substrate (such as those made from Cadmium Zinc Telluride ($Cd_{(1-x)}Zn_xTe$) semiconductor crystals or ZnTe materials), then it may be secured to the first and second electrodes 502 and 504 by indium bump(s). Alternatively, the photoconductor 506 may also be secured to the first and second electrodes 502 and 504 by a suitable adhesive, depending on the materials from which the photoconductor 506 and the first and second electrodes 502 and 504 are made. Other techniques known in the art may also be used to secure the photoconductor 506 to the first and second electrodes 502 and 504. Photoconductors and imagers made therefrom are well known in the art, and therefore would not be described in further details herein.

When using the flat panel imager 500, the first and second electrodes 502 and 504 are biased by a voltage source to create a potential difference or a bias between the first and second electrodes 502 and 504. The biased electrodes 502 and 504 create an electric field across the region between the first and second electrodes 502 and 504. When the photoconductor 506 is irradiated by x-ray, a response, such as electron hole pairs (EHPs) or charges, are generated and drift apart under the influence of the electric field across the region between the first and second electrodes 502 and 504. The charges are collected by the detector array 520, which includes a plurality of detector elements 522 arranged in a two-dimensional array. The detector elements 522 are configured to generate electric signals in response to the charges collected on the first electrode 502. In one embodiment, the detector elements 522 are amorphous silicon (a-Si:H) charge detectors. Each detector element 522 may have a storage capacitor to store the charge generated by the X-rays and collected by the first electrode 502. Each detector element 522 may also include a switching element, such as a thin film transistor (TFT), a switching diode, or the like, to access the collected charge by readout electoronics. Optionally the detector elements 522 can contain further components for signal or charge buffering and amplification. The detector elements 522 may also include polycrystalline silicon or organic active elements. Each of the detector elements 522 forms a pixel of the X-ray image generated using the detector array 520. The detector array 520 also includes a pixel access circuit (not shown) coupled to detector elements 522. The pixel access circuit accesses the detector elements 522 and reads the electric signals from the detectors elements 522. The process of accessing detector elements 522 and reading electric signals there from is similarly discussed previously with reference to FIG. 3. In one embodiment, pixel access circuit includes a gate driver that generates row access signals to sequentially access detector elements 522 by rows and reads electric signals out of detector elements 522 by columns. Each row access signal can access either a single row or multiple rows of detectors elements 522. Likewise, each read action can read electric signals from either a single column or a plurality of columns of the detectors elements 522.

Figure 6:
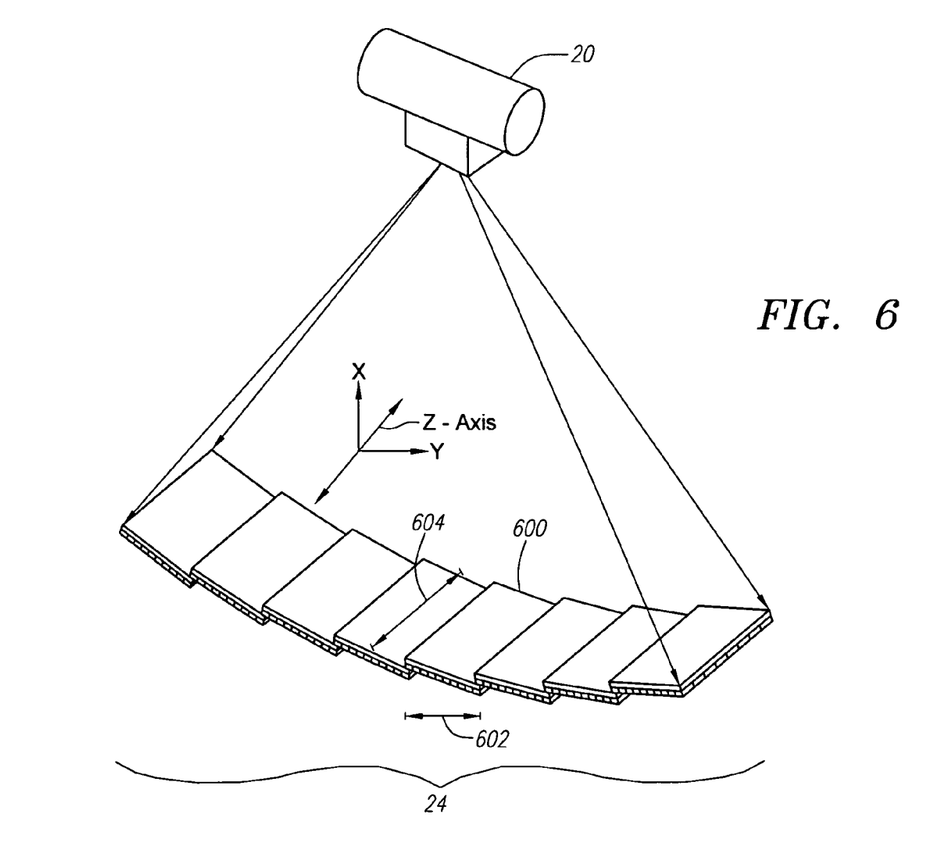
FIG. 6 shows an alternative embodiment of the detector of FIG. 1.

FIG. 6 shows another embodiment of the detector 24 that includes a plurality of imagers 600. In one embodiment, each imager 600 has a panel width 602 that is between 2 to 10 centimeters (cm), and a panel depth 604 that is between 20 to 60 cm, and more preferably, between 30 to 40 cm. However, each imager 600 may also have other dimensions in alternative embodiments. In the illustrated embodiment, each of the imagers 600 is stacked against an edge of a neighboring imager 600. This configuration is beneficial in that the imagers 600 provide a non-discontinuous surface to capture image signals, thereby preventing a gap in the collected image data. Alternatively, the imagers 600 may be positioned next to each other such that a substantially continuous surface can be formed. Although eight imagers 600 are shown, in alternative embodiments, the detector 24 may include one or other numbers of imagers 600, depending on a particular specification of the detector 24. In addition, although the imagers 600 collectively form a curvilinear profile of the detector 24, in alternative embodiments, the imagers 600 may collectively form an approximately straight surface or other profiles for the detector 24.

Constructing the detector 24 using a plurality of the imagers 600 has several advantages. First, the manufacturing cost of the detector 24 is reduced since it is easier and less expensive to manufacture a number of smaller imagers 600 than to manufacture a single imager of sufficient size that can meet the specification of the detector 24. In addition, the plurality of the imagers 600 provides another level of multiplexing in that signals from one or more lines of image elements 104 in one of the imagers 600 can be read simultaneously with signals from one or more lines of image elements 104 in another of the imagers 600 by the gate driver 112. In one embodiment, the gate driver 112 can be configured to read signals from the first two rows of all of the imagers 600 simultaneously, and then from the next two rows, etc., until signals from all the rows of the imagers 600 have been read. Such configuration provides a much higher frame rate for the detector 24, thereby allowing more image data to be collected in a given period.

For example, assuming that the detector 24 has fourteen imagers 600, each of which has fifty rows of image elements 104. In such case, if an average readout rate for a row is 40 microseconds, it will take 2000 microseconds (=40 microseconds×50 rows) to read signals from the entire detector 24, thereby providing 500 frame rate per second (½000 microseconds). If multiple rows readout scheme is used, e.g., assuming signals are read from every two rows simultaneously, it will take 1000 microseconds to read signals from the entire detector 24, thereby providing 1000 frame rate per second. Both of these configurations provide much better frame rate than conventional detectors that use a single row readout scheme for the entire detector. For example, using a conventional readout scheme, it will take 24000 microseconds (=40 microseconds×600 rows) to read signals from a detector that has the same number of rows (i.e., 600 rows) of image elements, providing only 41 frame rate per second. Those skilled in the art understand that the more the number of the flat panel imagers 600 used, the higher the frame rate that can be achieved.

Constructing the detector 24 using a plurality of the imagers 600 can also provide better resolution for images. For example, for a given prescribed frame rate, the detector 24 can be configured to provide better resolution by using more number of the imagers 600 that are smaller, but have lower pixel pitch. In one embodiment, the detector 24 includes twenty-four imagers 600, each of which has a panel width of approximately 2.5 centimeters and has a pixel pitch of approximately 380 um. Such configuration provides approximately the same frame rate, but a much higher resolution, as compared to a detector that includes fourteen imagers 600, with each imager 600 having a panel width of approximately 4.5 centimeters and a pixel pitch of approximately 500 um.

It should be noted that in the illustrated embodiment in which a plurality of the imagers 600 is used, the reading of signals is not limited to two or more rows at a time, and that the gate driver 112 can be configured to access one row of image elements 104 at a time. For example, in alternative embodiments, the gate driver 112 can be configured to read signals from the first rows of all of the imagers 600 simultaneously, and then from the second rows, etc., until signals from all the rows of the imagers 600 have been read.

Figure 7:
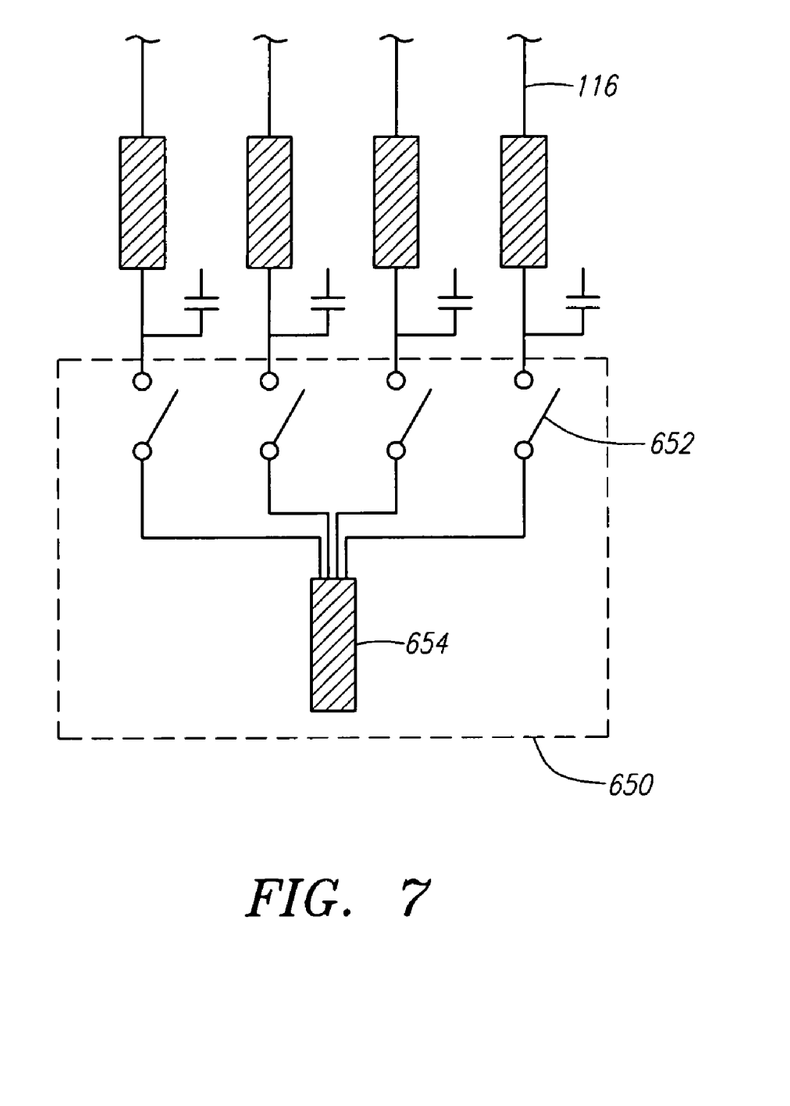
FIG. 7 shows a multiplex multi-row readout unit.

FIG. 7 shows a multiplex multi-row readout unit 650 that may be implemented in any of the above-described embodiments of imagers or in conventional imagers. The readout unit 650 includes a plurality of switches 652 connected to a common pad 654. Each of the switches 652 has a low resistance, thereby allowing signals from the image elements 104 to be read quickly. During use, the switches 652 switch consecutively to transmit signals to the common pad 654. The common pad 654 may be coupled to a device, such as an amplifier, a storage device, or a processor, which receives the signals. In the illustrated embodiment, the readout unit 650 includes four switches 652. However, the readout unit 650 may also include other numbers of switches 652 in alternative embodiments.

Computer System Architecture

Figure 8:
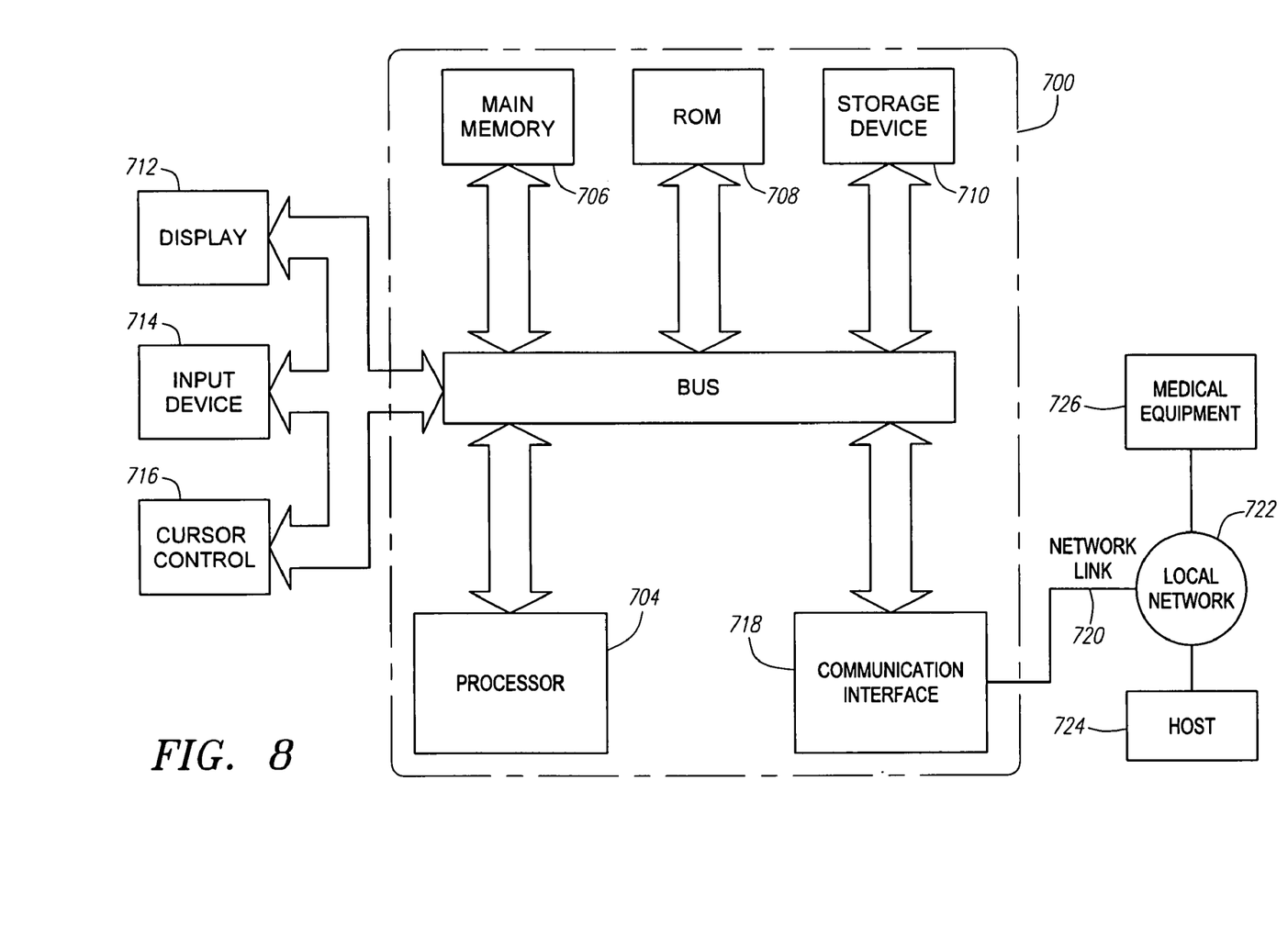
FIG. 8 is a diagram of a computer hardware system with which embodiments of the present invention can be implemented.

FIG. 8 is a block diagram that illustrates an embodiment of a computer system 700 upon which an embodiment of the invention may be implemented. Computer system 700 includes a bus 702 or other communication mechanism for communicating information, and a processor 704 coupled with the bus 702 for processing information. The processor 704 may be an example of the processor 54, or alternatively, an example of a component of the processor 54, of FIG. 1. The computer system 700 also includes a main memory 706, such as a random access memory (RAM) or other dynamic storage device, coupled to the bus 702 for storing information and instructions to be executed by the processor 704. The main memory 706 also may be used for storing temporary variables or other intermediate information during execution of instructions to be executed by the processor 704. The computer system 700 further includes a read only memory (ROM) 708 or other static storage device coupled to the bus 702 for storing static information and instructions for the processor 704. A data storage device 710, such as a magnetic disk or optical disk, is provided and coupled to the bus 702 for storing information and instructions.

The computer system 700 may be coupled via the bus 702 to a display 77, such as a cathode ray tube (CRT), for displaying information to a user. An input device 714, including alphanumeric and other keys, is coupled to the bus 702 for communicating information and command selections to processor 704. Another type of user input device is cursor control 716, such as a mouse, a trackball, or cursor direction keys for communicating direction information and command selections to processor 704 and for controlling cursor movement on display 77. This input device typically has two degrees of freedom in two axes, a first axis (e.g., x) and a second axis (e.g., y), that allows the device to specify positions in a plane.

The invention is related to the use of computer system 700 for collecting and processing image data. According to one embodiment of the invention, such use is provided by computer system 700 in response to processor 704 executing one or more sequences of one or more instructions contained in the main memory 706. Such instructions may be read into the main memory 706 from another computer-readable medium, such as storage device 710. Execution of the sequences of instructions contained in the main memory 706 causes the processor 704 to perform the process steps described herein. One or more processors in a multi-processing arrangement may also be employed to execute the sequences of instructions contained in the main memory 706. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 704 for execution. Such a medium may take many forms, including but not limited to, non-volatile media, volatile media, and transmission media. Non-volatile media includes, for example, optical or magnetic disks, such as the storage device 710. Volatile media includes dynamic memory, such as the main memory 706. Transmission media includes coaxial cables, copper wire and fiber optics, including the wires that comprise the bus 702. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 704 for execution. For example, the instructions may initially be carried on a magnetic disk of a remote computer. The remote computer can load the instructions into its dynamic memory and send the instructions over a telephone line using a modem. A modem local to the computer system 700 can receive the data on the telephone line and use an infrared transmitter to convert the data to an infrared signal. An infrared detector coupled to the bus 702 can receive the data carried in the infrared signal and place the data on the bus 702. The bus 702 carries the data to the main memory 706, from which the processor 704 retrieves and executes the instructions. The instructions received by the main memory 706 may optionally be stored on the storage device 710 either before or after execution by the processor 704.

The computer system 700 also includes a communication interface 718 coupled to the bus 702. The communication interface 718 provides a two-way data communication coupling to a network link 720 that is connected to a local network 722. For example, the communication interface 718 may be an integrated services digital network (ISDN) card or a modem to provide a data communication connection to a corresponding type of telephone line. As another example, the communication interface 718 may be a local area network (LAN) card to provide a data communication connection to a compatible LAN. Wireless links may also be implemented. In any such implementation, the communication interface 718 sends and receives electrical, electromagnetic or optical signals that carry data streams representing various types of information.

The network link 720 typically provides data communication through one or more networks to other devices. For example, the network link 720 may provide a connection through local network 722 to a host computer 724 or to a medical equipment 726. The data streams transported over the network link 720 can comprise electrical, electromagnetic or optical signals. The signals through the various networks and the signals on the network link 720 and through the communication interface 718, which carry data to and from the computer system 700, are exemplary forms of carrier waves transporting the information. The computer system 700 can send messages and receive data, including program code, through the network(s), the network link 720, and the communication interface 718.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. For example, the operations performed by the processor 54 can be performed by any combination of hardware and software within the scope of the invention, and should not be limited to particular embodiments comprising a particular definition of "processor". The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A radiation projection detector for generating signals in response to a radiation beam, the detector comprising a first imager, the first imager having:
   a conversion layer configured to generate light photons in response to a radiation;
   a photo detector array aligned with the conversion panel, the photo detector array comprises a plurality of lines of detector elements, each of the detector elements configured to generate a signal in response to the light photons received from the conversion layer; and
   an access circuit coupled to the photo detector array and configured to collect signals from two or more of the lines of detector elements simultaneously, wherein the access circuit is further configured to maintain the collected signals separated from each other to thereby allow the signals be individually processed.

2. The detector of claim 1, wherein the first imager further having a signal processing circuit coupled to the access circuit and configured to generate image data using the signals received by the access circuit.

3. The detector of claim 1, wherein the access circuit is configured to collect signals from two of the lines of detector elements simultaneously.

4. The detector of claim 1, wherein the access circuit is configured to collect signals from four of the lines of detector elements simultaneously.

5. A radiation projection detector for generating signals in response to a radiation beam, the detector comprising a first imager, the first imager having:
   a conversion layer configured to generate light photons in response to a radiation;
   a photo detector array aligned with the conversion panel, the photo detector array comprises a plurality of lines of detector elements, each of the detector elements configured to generate a signal in response to the light photons received from the conversion layer;
   an access circuit coupled to the photo detector array and configured to collect signals from two or more of the lines of detector elements simultaneously; and
   a second imager positioned adjacent to the first imager.

6. The detector of claim 5, wherein an edge of the second imager is positioned below an edge of the first imager.

7. The detector of claim 5, wherein an edge of the second imager is positioned next to an edge of the first imager.

8. The detector of claim 5, wherein the access circuit is further configured to collect signals from two or more of the lines of detector elements of the second imager simultaneously.

9. The detector of claim 5, wherein the access circuit is further configured to collect signals from both the first and the second imagers simultaneously.

10. The detector of claim 1, wherein the plurality of lines of detector elements comprises a plurality of rows or columns of detector elements.

11. A radiation projection detector for generating signals in response to a radiation beam, the detector comprising a first imager, the first imager having:
    a photoconductor layer configured to generate a charge in response to a radiation;
    a detector array aligned with the photoconductor layer, the detector array comprises a plurality of lines of detector elements, each of which configured to generate a signal in response to the charge received from the photoconductor layer; and
    an access circuit coupled to the detector array and configured to collect signals from two or more of the lines of detector elements simultaneously.

12. The detector of claim 11, wherein the first imager further having a signal processing circuit coupled to the access circuit and configured to generate image data using the signals received by the access circuit.

13. The detector of claim 11, wherein the access circuit is configured to collect signals from two of the lines of detector elements simultaneously.

14. The detector of claim 11, wherein the access circuit is configured to collect signals from four of the lines of detector elements simultaneously.

15. The detector of claim 11, further comprising a second imager positioned adjacent to the first imager.

16. The detector of claim 15, wherein an edge of the second imager is positioned below an edge of the first imager.

17. The detector of claim 15, wherein an edge of the second imager is positioned next to an edge of the first imager.

18. The detector of claim 15, wherein the access circuit is further configured to collect signals from two or more of the lines of detector elements of the second imager simultaneously.

19. The detector of claim 15, wherein the access circuit is further configured to collect signals from both the first and the second imagers simultaneously.

20. The detector of claim 11, wherein the plurality of lines of detector elements comprises a plurality of rows or columns of detector elements.

21. A radiation projection detector for generating signals in response to a radiation beam, the detector comprising:
    a first imager;
    a second imager; and
    an access circuit configured to collect signals from the first imager and the second imager simultaneously.

22. The detector of claim 21, wherein an edge of the second imager is positioned below an edge of the first imager.

23. The detector of claim 21, wherein an edge of the second imager is positioned next to an edge of the first imager.

24. The detector of claim 21, wherein each of the first and second imagers comprises a conversion layer configured to generate light photons in response to a radiation.

25. The detector of claim 24, wherein each of the first and second imagers further comprises:
    a photo detector array aligned with the conversion panel, the photo detector array comprises a plurality of lines of detector elements, each of which configured to generate a signal in response to the light photons received from the conversion layer;
    wherein the access circuit is coupled to the photo detector array of each of the first and second imagers.

26. The detector of claim 25, wherein the access circuit is configured to collect signals from one line of the detector elements of each of the first and second imagers at a time.

27. The detector of claim 25, wherein the access circuit is configured to collect signals from more than one line of the detector elements of each of the first and second imagers at a time.

28. The detector of claim 21, wherein each of the first and second imagers comprises a photoconductor layer configured to generate a charge in response to a radiation.

29. The detector of claim 28, wherein each of the first and second imagers further comprises:
   a detector array aligned with the photoconductor layer, the detector array comprises a plurality of lines of detector elements, each of which configured to generate a signal in response to the charge received from the photoconductor layer;
   wherein the access circuit is coupled to the detector array of each of the first and second imagers.

30. The detector of claim 29, wherein the access circuit is configured to collect signals from the detector elements of each of the first and second imagers one line at a time.

31. The detector of claim 29, wherein the access circuit is configured to collect signals from the detector elements of each of the first and second imagers more than one line at a time.

32. A method for collecting signals from a detector, the detector having a plurality of lines of image elements, each of which having a transistor gate, the method comprising:
   sending a control signal to a gate driver to select transistor gates for two or more lines of image elements from which signals are to be collected; and
   simultaneously passing signals from the two or more lines of image elements to charge amplifiers that are coupled to the image elements.

33. The method of claim 32, further comprising generating the signals.

34. The method of claim 33, wherein the generating the signals comprises:
   receiving an x-ray radiation;
   generating photons in response to at least a portion of the x-ray radiation; and
   producing the signals in response to the photons.

35. The method of claim 33, wherein the generating the signals comprises:
   receiving an x-ray radiation;
   generating electron-hole-pairs in response to at least a portion of the x-ray radiation; and
   producing the signals in response to the electron-hole-pairs.

36. A computer readable medium having a set of stored instructions, the execution of which causes a process for collecting signals from a detector to be performed, the detector having a plurality of lines of image elements, each of the image elements having a transistor gate, the process comprising:
   sending a control signal to a gate driver to select transistor gates for two or more lines of image elements from which signals are to be collected; and
   simultaneously passing signals from the two or more lines of image elements to charge amplifiers that are coupled to the image elements.

37. The computer readable medium of claim 36, wherein the process further comprising generating the signals.

38. The computer readable medium of claim 37, wherein the generating the signals comprises:
   receiving an x-ray radiation;
   generating photons in response to at least a portion of the x-ray radiation; and
   producing the signals in response to the photons.

39. The computer readable medium of claim 37, wherein the generating the signals comprises:
   receiving an x-ray radiation;
   generating electron-hole-pairs in response to at least a portion of the x-ray radiation; and
   producing the signals in response to the electron-hole-pairs.

40. A system for collecting signals from a detector, the detector having a plurality of lines of image elements, each of which having a transistor gate, the system comprising:
   means for sending a control signal to a gate driver to select transistor gates for two or more lines of image elements from which signals are to be collected; and
   means for simultaneously passing signals from the two or more lines of image elements to charge amplifiers that are coupled to the image elements.

41. A method for collecting signals from a detector, the detector having a plurality of imagers, each of the imagers having a plurality of lines of image elements, the method comprising:
   sending a control signal to a gate driver to select one or more lines of image elements on each of the plurality of the imagers from which signals are to be collected; and
   simultaneously passing signals from the selected one or more lines of image elements on each of the plurality of the imagers to charge amplifiers that are coupled to the image elements.

42. The method of claim 41, wherein each of the plurality of imagers comprises a flat panel imager.

43. The method of claim 41, wherein the sending comprises sending a control signal to a gate driver to select one line of image elements on each of the plurality of the imagers.

44. The method of claim 41, wherein the sending comprises sending a control signal to a gate driver to select a plurality of lines of image elements on each of the plurality of the imagers.

45. The method of claim 44, wherein the plurality of lines of image elements comprises four lines of image elements.

46. The method of claim 41, further comprising generating the signals.

47. The method of claim 46, wherein the generating the signals comprises:
   receiving an x-ray radiation;
   generating photons in response to at least a portion of the x-ray radiation; and
   producing the signals in response to the photons.

48. The method of claim 46, wherein the generating the signals comprises:
   receiving an x-ray radiation;
   generating electron-hole-pairs in response to at least a portion of the x-ray radiation; and
   producing the signals in response to the electron-hole-pairs.

49. A computer readable medium having a set of stored instructions, the execution of which causes a process for collecting signals from a detector to be performed, the detector having a plurality of imagers, each of the imagers having a plurality of lines of image elements, the process comprising:
   sending a control signal to a gate driver to select one or more lines of image elements on each of the plurality of the imagers from which signals are to be collected; and
   simultaneously passing signals from the selected one or more lines of image elements on each of the plurality of the imagers to charge amplifiers that are coupled to the image elements.

50. A system for collecting signals from a detector, the detector having a plurality of imagers, each of the imagers having a plurality of lines of image elements, the system comprising:

means for sending a control signal to a gate driver to select one or more lines of image elements on each of the plurality of the imagers from which signals are to be collected; and means for simultaneously passing signals from the selected one or more lines of image elements on each of the plurality of the imagers to charge amplifiers that are coupled to the image elements.

* * * * *